United States Patent [19]

Kleemann et al.

[11] 4,025,540

[45] May 24, 1977

[54] PROCESS FOR THE PRODUCTION OF PURE CARBOXYLIC ACID-1-MONOGLYCERIDES

[75] Inventors: Axel Kleemann; Heinz Kolb, both of Hanau; Anne Rindfuss, Frankfurt; Gerd Schreyer, Hanau; Ludwig-Karl Schwörzer, Illertissen; Gregor Schuster, Neu-Ulm, all of Germany

[73] Assignee: Deutsche Gold- und Silber-Scheideanstalt vormals Roessler, Frankfurt, Germany

[22] Filed: Oct. 16, 1975

[21] Appl. No.: 623,076

[30] Foreign Application Priority Data

Oct. 19, 1974 Germany .................. 2449847

[52] U.S. Cl. .................. 260/410.7; 260/410.6; 260/468 R; 260/476 R; 260/485 G; 260/475 P; 260/469; 260/496

[51] Int. Cl.² .................. C09F 5/08; C11C 3/00; C11C 3/02

[58] Field of Search ......... 260/410.6, 410.7, 468 R, 260/476 R, 485 G, 475 P, 469, 496

[56] References Cited

UNITED STATES PATENTS

| | | | |
|---|---|---|---|
| 2,251,693 | 8/1941 | Richardson | 260/410.7 |
| 2,789,119 | 4/1957 | Sully | 260/410.7 |
| 2,875,221 | 2/1959 | Birnbaum | 260/410.7 |
| 2,910,490 | 10/1959 | Malkemus | 260/410.6 |
| 3,079,412 | 2/1963 | Chang | 260/410.7 |
| 3,083,216 | 3/1963 | Alsop et al. | 260/410.7 |
| 3,102,129 | 8/1963 | Birnbaum | 260/410.6 |
| 3,595,888 | 7/1971 | Reiser | 260/410.7 |

*Primary Examiner*—Winston A. Douglas
*Assistant Examiner*—John F. Niebling
*Attorney, Agent, or Firm*—Cushman, Darby & Cushman

[57] ABSTRACT

Very pure carboxylic acid-1-monoglycerides are prepared by reacting a carboxylic acid with glycidol at a temperature of 80° to 200° C. in the presence of a basic alkali metal or alkaline earth metal compound as a catalyst in the presence of an inert solvent which forms a homogeneous solution with the reactants at the reaction temperature.

18 Claims, No Drawings

PROCESS FOR THE PRODUCTION OF PURE CARBOXYLIC ACID-1-MONOGLYCERIDES

Carboxylic acid-1-monoglycerides, especially those derived from fatty acids with 8–20 carbon atoms, today are of great technical and industrial importance as non-ionic surface active compounds, as, for example, emulsifiers, solvent aids, wetting agents, the base of salves, and also as intermediate products. A large number of processes are known for their production. Thus, for example, they can be obtained by glycerinolysis of triglycerides (fats), hydrolysis of the isopropylidene derivatives, acylation of glycerine with fatty acid chlorides, direct esterification of fatty acids with glycerine, glycerinolysis of alkyl esters of fatty acids, etc. However, according to all of these processes there are not obtained pure fatty acid-1-monoglycerides. The reaction products have a maximum 1-monoglyceride content of 60–70% and still contain noteworthy amounts of glycerine, isomeric 2-monoglycerides, as well as di- and tri-glycerides, and also in many cases small amounts of polyglycerine or polyglycerine esters. To recover a high percentage of 1-monoglyceride with a purity of 85–95% from the raw material, it is necessary to subject the latter to a molecular distillation. The molecular distillation, as is know, is a purification which is technically expensive and costly. For the installation of fatty acid-1-monoglycerides, for example as emulsifiers in foods, however, such high percentage products are necessary.

A further process for the recovery of 1-monoglycerides depends on the reaction of glycidol with the corresponding carboxylic acid according to the following equation (1):

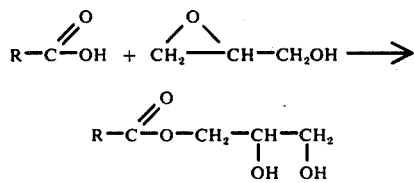

(1)

To be sure this reaction has been known for a long time and has been the object of numerous published patent applications and patents. However, until now no one knew how to obtain carboxylic acid-1-monoglycerides in this manner with a high degree of purity comparable to a product made by molecular distillation.

According to Malkemus, U.S. Pat. No. 2,910,490, an 88.7% stearic acid-1-monoglyceride should be formed in the solvent-free reaction of stearic acid with glycidol in equivalent amounts at 110°–115° C. (4 hours) and in the presence of 1% tetraethyl ammonium bromide. The entire disclosure of Malkemus is hereby incorporated by reference and relied upon. E. Ulsperger in Tenside Vol. 2, pages 332–333 (1965), describes the same reaction at 125°–135° C. (2 hours reaction time) in the presence of 1/100 mole of sodium methylate as a catalyst according to which there should be formed an 81.6% stearic acid-1-monoglyceride. This reaction was also carried out with other fatty acids. In Dalby, U.S. Pat. No. 3,251,870, it is stated that 1-monoglycerides are formed by the solvent free reaction of carboxylic acids with glycidol at 70° C. (without catalyst, reaction time about 30 minutes). The entire disclosure of Dalby is hereby incorporated by reference and relied upon. German Offenlegungsschrift No. 1,443,596 describes carrying out this reaction in an alkali salt containing aqueous solution at 80° C.

In all of these publications there is not given the information as to what method was employed to exactly determine the content of carboxylic acid-1-monoglyceride. Now and then to characterize the degree of purity of the reaction product obtained, reference is made to saponification number or ester number, acid number, hydroxyl number, and melting point. However, these methods are just as little suited as the determination of the vicinal hydroxyl groups by means of periodic acid for exact analysis of the reaction product, since besides the main reaction corresponding to equation (1) there are also the following side reactions (2) to (5):

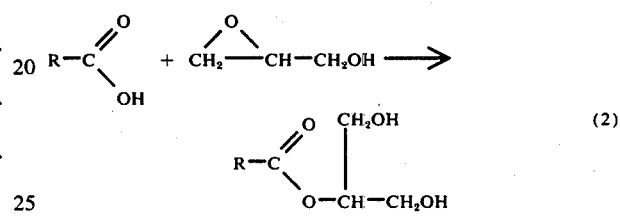

(2)

Carboxylic acid-2-monoglyceride

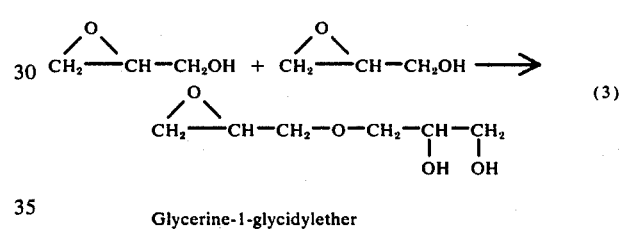

(3)

Glycerine-1-glycidylether

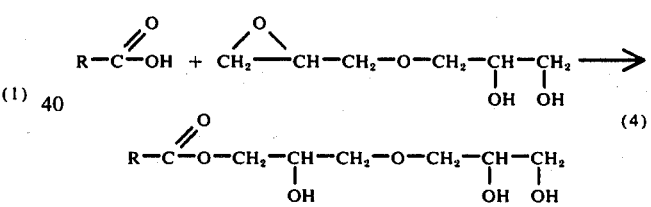

(4)

Diglycerine-1-monocarboxylic acid

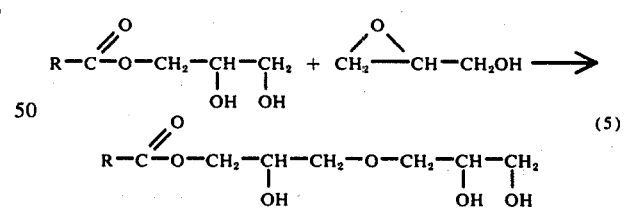

(5)

Besides reactions (2) to (5), there also occurs to a small extent polyglycidol formation and through intra- or intermolecular acyl group migration there are formed under the reaction conditions (higher temperatures, alkali medium) free glycerine as well as di- and triglycerides.

It is evident that these byproducts simulate higher 1-monoglyceride contents in all of the named methods of analysis. This also happens in the periodic splitting of the vicinal glycol groups since these are also present in glycerine and the diglycerine-1-carboxylic acid esters formed in equations (4) and (5). Therefore, an unequivocal statement of the true degree of purity of the product is not possible with these analytical methods, see Example 1 in this regard.

On the contrary, the exact composition of the addition products of carboxylic acids and glycidol can be ascertained by the following method, namely, by column chromatography.

ABSORPTION AGENT

The silica gel (for partition chromatography according to Merck, finely divided) is first dried at about 500° C. and then covered with 7% of water.

COLUMN

Inner diameter 2 cm., length about 30 cm; 30 grams of silica gel were washed with petroleum ether into the column at the opened cock in such manner that the silica gel always remained covered with petroleum ether.

PROCEDURE 1 gram of material is weighed in a 50 ml beaker, dissolved in 15 ml of chloroform (if necessary with heating) and supplied to the column. From a dropping funnel, which is suitably over the column, there is now dropped 200 ml of benzene. The eluate is collected in a preweighed 500 ml Erlenmeyer flask. The velocity of flow is so regulated that about 2-3 ml of solvent per minute flows through the column, whereby perhaps some pressure ($CO_2$ or $N_2$ bomb) is necessary. When all of the benzene is run out of the dropping funnel elution is further carried out with 200 ml of a benzene-ether mixture (180 ml benzene + 20 ml diethyl ether) and the Erlenmeyer flask, which serves as a receiver, exchanged for another. If this amount of solvent also flows through the column, then elution is carried out with 200 ml of ether-alcohol (170 ml of diethyl ether, dried over calcium chloride, 30 ml ethanol) and the receiver exchanged again, see Example 2.

The three fractions are carefully evaporated on the steam bath, the last solvent vapor blown away with dry nitrogen and the Erlenmeyer flask dried for 30 minutes before the weighing at 105° C. in a drying cabinet. In the first Erlenmeyer flask there is found the triglyceride, in the second the diglyceride, and in the third the monoglyceride.

If these methods of determination are applied to the reaction products of glycidol and stearic acid produced by the known processes, for example, according to Ulsperger (loc. cit.), there is made the surprising determination, that the products only contain about 70% stearic acid-1-monoglyceride besides 3-6% of stearic acid-2-monoglyceride and about 10-14% polyglycerine or stearic acid-polyglycerine esters (predominantly diglycerine derivatives) as well as up to 3% glycerine and di- or tristearin.

Somewhat more favorable values are obtained if the reaction is undertaken in such manner that stearic acid and catalyst (0.4 weight % 50% aqueous NaOH tested) are present, heated to 130°-140° C. and glycide (1.05 mole per mole of stearic acid; with equimolar amounts there are obtained products with similarly high content of polyglycerine esters, but substantially higher acid number) dropped in the course of 20-60 minutes.

After a further 30-60 minutes at this temperature the glycidol reaction is ended.

Contrary to the state of the art, it has now been found that very pure carboxylic acid-1-monoglycerides can be produced without molecular distillation, if the known reaction of carboxylic acids with glycidol is carried out at temperatures from 80°-200° C. with basic reacting alkali metal or alkaline earth metal compounds as catalysts but in the presence of an inert solvent which forms a homogeneous solution with the reactants at the reaction temperature involved.

Surprisingly in the presence of these solvents the polyglycerine ester portion is greatly reduced so that the carboxylic acid-1-monoglyceride obtained has the purity previously obtainable only by the molecular distillation of the recovered product, see, for example, Example 1.

There can be employed as solvents in the invention organic solvents which are inert to the starting materials and end products, which have a certain dissolving power for the reactants and which at lower temperatures of about 0°-80° C. only keep in solution small amounts of the 1-monoglycerides formed. Among these solvents are aromatic hydrocarbons with 6 to 9 carbon atoms, e.g., benzene, toluene, o-xylene, ethyl benzene, m-xylene, p-xylene, isopropyl benzene, propyl benzene, halogenated toluene, e.g., trifluoromethyl benzene (also called benzotrifluoride or $\alpha,\alpha,\alpha$-trifluorotoluene), chlorobenzene, fluorobenzene, 1,2-dichlorobenzene, benzotrichloride. The preferred solvents of these classes are benzene, toluene and benzotrifluoride.

Also, there can be used aliphatic ketones with 3 to 9 carbon atoms such as acetone, methyl ethyl ketone, dibutyl ketone, methyl butyl ketone and especially methyl isopropyl ketone, methyl isobutyl ketone, diethyl ketone and di-isobutyl ketone.

Likewise, there can be used aliphatic ethers with at least 6 carbon atoms, e.g., dipropyl ether, diamyl ether, diisoamyl ether and especially di-isopropyl ether.

There can also be used mixtures of solvents.

Especially preferred as a solvent is toluene.

The process can be carried out either at normal pressure (atmospheric pressure) or at superatmospheric pressures up to 100 atmospheres, with or without addition of an inert gas. In the autoclave, the pressure of the solvent is present.

To prepare the monoglyceride, there can be used all mono and polybasic carboxylic acids which are known in the art to react with glycidol, i.e., saturated and unsaturated, straight and branched, even and odd number of carbon atoms, aliphatic, aromatic and hydroaromatic carboxylic acids with 7 to about 20 carbon atoms. Especially preferred are fatty acids having a chain length of 8 to 18 carbon atoms. Examples of suitable acids are caprylic acid, decanoic acid, lauric acid, myristic acid, palmitic acid, stearic acid, eicosanic acid, oleic acid, palmitoleic acid, tall oil acids, benzoic acid, 4-chlorobenzoic acid, 2,4-dichlorobenzoic acid, t-butyl benzoic acid, ricinoleic acid, cyclohexane carboxylic acid, toluic acid, adipic acid, pimelic acid, azelaic acid, napthoic acid, phthalic acid, benzene tricarboxylic acid, benzene tetracarboxylic acid, cinnamic acid, phenylacetic acid, 2-ethyl caprylic acid, 2,4-dimethyl caprylic acid and enanthic acid.

The molar ratio of glycidol:carboxylic acid can be varied in the range 0.8-1.3, for example. The preferred ratio is from 1.0-1.1:1.

The solvent employed is conveniently used in an amount from equal to about four times the sum of the reactants, preferably in about 2-3 times the amount. However, smaller and larger amounts are also possible and the amount of solvent is not critical.

As catalysts there can be used, example, strong bases such as lithium hydroxide, sodium hydroxide, potassium hydroxide or barium hydroxide in anhydrous form or in the form of an aqueous concentrated solution (up to about 50% except for barium hydroxide which has a maximum solubility of 4%) as well as sodium alcoholates such as sodium methylate, sodium ethylate, potassium methylate, magnesium alcoholates, e.g., magnesium ethylate, or calcium alcoholates, e.g., calcium ethylate.

The catalysts are conveniently used in an amount of 0.1 to 1.0 weight %, preferably in an amount of 0.2–0.4 weight %, based on the sum of the reactants.

However, there can also be added other catalysts known to be suitable in this type of process. Especially preferred is anhydrous sodium hydroxide, preferably in an amount of 0.2–0.4 weight %, based on the sum of the reactants.

The reactants can be mixed with the solvent and catalyst before the actual reaction. It has also proven advantageous to first mix the carboxylic acid, solvent and catalyst and to gradually add the glycidol only after heating the mixture to the reaction temperature.

The preferred reaction temperature is between 110° and 160° C. Elevated pressure is preferably used if the boiling point of the solvent is below that of the reaction temperature employed. The temperature can be varied, however, beyond the preferred range.

The process can be carried out either continuously, for example in a loop reactor, or discontinuously, i.e., batchwise.

The industrial advantage of the process of the invention, as already stated, is in the possibility of obtaining products of the same purity as in a molecular distillation but using a much simpler procedure.

The monoglycerides obtained have food grade purity and can be added directly for emulsifiers in foods, entirely apart from their ability to be used elsewhere.

Unless otherwise indicated, all parts and percentages are by weight.

The invention will be further explained in connection with the following examples.

EXAMPLE 1

0.4 mole of stearic acid (114 grams) were suspended in 190 grams toluene and after addition of 0.29 grams of sodium hydroxide filled into a V4 A steel autoclave. After heating to 160° C. there was pumped in within 8 minutes a solution of 29.6 grams of glycidol (0.4 mole) in 50 grams of toluene and subsequently the pump line was rinsed with 50 grams of toluene. After a further 30 minutes at 160° C. the mixture was cooled to about 70° C. and neutralized (at will lactic acid or phosphoric acid). A glycidol determination showed a reaction of 91%. After cooling to room temperature the precipitated product was filtered off with suction (in later experiments it was found more favorable to use a centrifuge) and washed three times, each time with 50 ml of toluene (for removal of unreacted glycidol and traces of acid). After drying of the product in a vacuum drying cabinet at 50° C. over paraffin oil there were obtained 97 grams of stearic acid monoglyceride (67.6% of theory) with the following properties.

| Melting Point | 72–73° C. |
| --- | --- |
| Acid Number | 2.6 |
| Saponification Number | 162 |
| Content of 1-monoglyceride according to periodate analysis (without previous column chromatographic separation) | 99.4% |

After quantitative column chromatographic separation, the following composition was obtained:

| Stearic acid-1-monoglyceride | 93.1% |
| --- | --- |
| Stearic acid-2-monoglyceride | 2.0% |
| Distearin | 0.9% |
| Tristearin | 0.8% |
| Glycerine | 0.4% |
| Polyglycerine & polyglycerine esters | 2.9% |
| | 100.1% |

EXAMPLE 2

(Comparison Example Without Inert Solvent)

0.4 mole of stearic acid were treated with 0.6 gram of 50% aqueous NaOH, within 20 minutes —while stirring well— 31.2 grams of glycidol (0.42 mole) dropped in. After 30 minutes, 98% of the glycidol had reacted and the mixture was cooled to 80° C. and neutralized.

A periodic acid splitting showed a stearic acid-1-monoglyceride content of 83.4%. After column chromatographic separation, the following composition was obtained:

| Stearic acid-1-monoglyceride | 70.4% |
| --- | --- |
| Stearic acid-2-monoglyceride | 3.1% |
| Distearin | 12.5% |
| Tristearin | 0.7% |
| Glycerine | 1.7% |
| Polyglycerine + polyglycerine esters | 12.3% |

EXAMPLE 3

0.4 mole of stearic acid were heated to boiling (about 113° C.) under reflux with 280 grams of toluene and 0.29 gram of NaOH (water free) and, in the course of 20 minutes, 31.2 grams of glycidol dropped in. After a further 5 hours at this temperature, the glycidol was 99% reacted and the reaction ended. After working as in Example 1, there were obtained 123.5 grams (86%) of monostearin having the following properties:

| Melting Point | 71–72° C. |
| --- | --- |
| Acid Number | 2.0 |
| Saponification Number | 162 |
| Content of 1-monoglyceride according to periodate determination | 98.1% |

After column chromatographic separation, the following composition was obtained:

| Stearic acid-1-monoglyceride | 92.0% |
| --- | --- |
| Stearic acid-2-monoglyceride | 3.2% |

-continued

| | |
|---|---|
| Distearin | 0.9% |
| Tristearin | 0.5% |
| Glycerine | 0.2% |
| Polyglycerine + polyglycerine esters | 3.4% |

EXAMPLE 4

The experiment was carried out under the same conditions as in Example 3 but using a molar ratio of glycidol:stearic acid of 1.3:1. After 3 hours the amount of glycidol equivalent to the stearic acid had reacted and the mixture was cooled and worked up in a manner analogous to Example 1. There were obtained 116 grams of monostearin (80.9% yield) with the following properties:

| | |
|---|---|
| Melting Point | 72–73° C. |
| Acid Number | 2.0 |
| Saponification Number | 159 |
| Content of 1-monoglyceride according to periodate determination | 100.9% |

After column chromatographic separation, the following composition was obtained:

| | |
|---|---|
| Stearic Acid-1-monoglyceride | 93.2% |
| Stearic Acid-2-monoglyceride | 2.1% |
| Distearin | 1.4% |
| Tristearin | 0.8% |
| Glycerine | 0.2% |
| Polyglycerine + polyglycerine esters | 2.6% |

EXAMPLE 5

The experiment was carried out under the conditions of Example 3 but there were added only 0.4 mole of glycidol (29.6 grams) which corresponds to a molar ratio of 1.0:1.0. After working up in a manner analogous to Example 1, there was obtained 97.6 grams of monostearine (68% yield).
Properties:

| | |
|---|---|
| Melting Point | 71–72° C. |
| Acid Number | 2.8 |
| Saponification Number | 166 |
| Content of -1-monoglyceride according to periodate analysis | 102.8% |

Column chromatographic separation obtained:

| | |
|---|---|
| Stearic Acid -1-monoglyceride | 94.4% |
| Stearic Acid -2-monoglyceride | 2.6% |
| Distearin | 0.4% |
| Tristearin | 0.1% |
| Glycerine | 0.2% |
| Polyglycerine + polyglycerine esters | 2.6% |

EXAMPLES 6–9

In a manner analogous to Example 1 there were reacted lauric acid, myristic acid, palmitic acid, and 2,4-dichlorobenzoic with glycidol in the mole ratio 1:1 in toluene (toluene double the amount of the reactants) in the presence of 0.2 weight % of water free NaOH at 160° C. under pressure (30 minutes reaction time). The results, each time with 0.4 mole of reactants are set forth in the following table:

| Example | Acid Component | 1-Monoglyceride Content 1% | M.P. ° C. | Yield (%) |
|---|---|---|---|---|
| 6 | Lauric Acid | 95.7 | 61–62 | 63 |
| 7 | Myristic Acid | 96.3 | 66–68 | 70 |
| 8 | Palmitic Acid | 94.5 | 72–73 | 63.5 |
| 9 | 2,4-Dichlorobenzoic Acid | 87.2 | 69–70 | 65 |

EXAMPLES 10–13

In a manner analogous to Example 1, stearic acid was reacted with glycidol in the molar ratio of 1:1 in benzene, methyl isobutyl ketone, diisopropyl ether and trifluoromethyl benzene (in each case the solvent was double the amount of the reactants) in the presence of 0.2 weight % water free NaOH at 160° C. under autogenous pressure (30 minutes reaction time). The results, each time with 0.4 mole of reactants are set forth in the following table:

| Example | Solvent | 1-Monoglyceride Content (%) | Yield (%) |
|---|---|---|---|
| 10 | Benzene | 91.3 | 71.4 |
| 11 | Methyl isobutyl ketone | 87.4 | 61.4 |
| 12 | Diisopropyl ether | 88.8 | 68.0 |
| 13 | $\alpha,\alpha,\alpha$-trifluoromethyl benzene | 85.4 | 88.0 |

The process can comprise, consist essentially of or consist of the steps set forth and the composition employed can comprise, consist essentially of or consist of the materials set forth.

What is claimed is:

1. In a process for the product of a very pure carboxylic acid-1-monoglyceride comprising reacting a carboxylic acid having 7 to 20 carbon atoms with glycidol at 80° to 200° C. in the presence of a basic reacting alkali metal or alkaline earth metal compound as a catalyst the improvement comprising conducting said reaction in an inert solvent which forms a homogeneous solution with reactants at said temperature said solvent being selected from the group consisting of an aromatic hydrocarbon, a halogenated benzene, a halogenated toluene, an aliphatic ketone having 3 to 9 carbon atoms and an aliphatic ether having at least 6 carbon atoms.

2. The process of claim 1 wherein the acid is an aliphatic, aromatic or cyclohexane carboxylic acid.

3. The process of claim 2 wherein the acid is a fatty acid.

4. The process of claim 3 wherein the fatty acid has a chain length of 8–18 carbon atoms.

5. The process of claim 4 wherein the fatty acid is a saturated fatty acid having 12 to 18 carbon atoms.

6. The process of claim 1 wherein the temperature is 110°–160° C.

7. The process of claim 1 wherein the mole ratio of glycidol to carboxylic acid is 0.8°–1.3:1.

8. The process of claim 1 wherein the amount of solvent is 1 to 4 times the total amount of reactants.

9. The process of claim 1 wherein the solvent is an aromatic hydrocarbon, an aliphatic ketone having 3 to 9 carbon atoms or an aliphatic ether having at least 6 carbon atoms.

10. The process of claim 9 wherein the solvent is an aromatic hydrocarbon.

11. The process of claim 10 wherein the solvent is toluene.

12. The process of claim 9 wherein the solvent is a dialkyl ketone having 3 to 9 carbon atoms.

13. The process of claim 12 wherein the solvent is methyl isobutyl ketone.

14. The process of claim 9 wherein the solvent is a dialkyl ether having at least 6 carbon atoms.

15. The process of claim 14 wherein the solvent is diisopropyl ether.

16. The process of claim 1, wherein the mole ratio of glycidol to carboxylic acid is 0.8–1.3:1 and the amount of solvent is 1 to 4 times the total amount of reactants.

17. The process of claim 16, wherein the catalyst is 0.1 to 1.0% of the total amount of reactants.

18. The process of claim 17, wherein the acid is a fatty acid having 8 to 18 carbon atoms.

* * * * *